US 6,699,505 B2

United States Patent
Shastri et al.

(10) Patent No.: US 6,699,505 B2
(45) Date of Patent: Mar. 2, 2004

(54) METHOD OF INCREASING THE EFFICACY OF ANTIBIOTICS BY COMPEXING WITH CYCLODEXTRINS

(75) Inventors: Venkatram R. Shastri, Lower Gwynedd, PA (US); Isaac Yue, Midland, MI (US); Patrice Hildgen, Laval (CA); Ruben Dario Sinisterra, Belo Horizonte (BR); Robert Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/981,655

(22) Filed: Oct. 17, 2001

(65) Prior Publication Data

US 2003/0078215 A1 Apr. 24, 2003

Related U.S. Application Data

(60) Provisional application No. 60/241,054, filed on Oct. 17, 2000.

(51) Int. Cl.[7] .................................................. A61K 9/14
(52) U.S. Cl. ...................... 424/486; 424/484; 424/488; 424/422; 424/426; 514/54; 514/58
(58) Field of Search ................. 424/484, 488, 424/486, 422, 426; 514/54, 58, 772.1

(56) References Cited

U.S. PATENT DOCUMENTS

| | | | |
|---|---|---|---|
| 5,472,954 A | * | 12/1995 | Loftsson ..................... 514/458 |
| 5,624,914 A | * | 4/1997 | Patel et al. .................. 514/54 |
| 6,046,177 A | | 4/2000 | Stella et al. ................. 514/58 |
| 6,048,736 A | * | 4/2000 | Kosak ......................... 436/536 |

FOREIGN PATENT DOCUMENTS

| | | |
|---|---|---|
| EP | 0 306 455 | 3/1989 |
| EP | 3 350 147 | 1/1990 |
| WO | WO 98/56888 | 12/1998 |
| WO | WO-99/61062 A1 * | 12/1999 |

OTHER PUBLICATIONS

Cserháti, et al., "Modification of the Apparent Lipophilicity of Steroidal Drugs with Gamma–Cyclodextrin", *European Journal of Pharmaceuticals and Biopharmaceutics*, 46:153–159, 1998.

Irie, et al., "Amorphous Water–Soluble Cyclodextrin Derivatives: 2–Hydroxyethyl, 3–Hydroxporpyl, 2–Hydroxyisobutyl, and Carboxamidomethyl Derivatives of –Cyclodextrin", Pharmaceutical Research, 5(11): 713–717, 1988.

Kawashima, Y., "Aqueous Preparation" Japanese Abstract 1989.

Kinoshita, T. "Medical Material for External Use", Japanese Abstract 1986.

Müller, et al., "Hydroxypropyl– –Cyclodextrin Derivatives: Influence of Average Degree of Substitution on Complexing Ability and Surface Activity", *Journal of Pharmaceutical Sciences*, 75(6): 571–572, 1986.

Müller, et al., "Change of Phase–Solubility Behavior by Gamma–Cyclodextrin Derivatization", *Pharmaceutical Research* 309–310, 1985.

Nishi, K "Pharmaceutical Water–Based Preparation", Japanese Abstract 1985.

Pagington, J. "–Cyclodextrin: The Success of Molecular Inclusion", Chemistry in Britain, 455–458, 1987.

Qi, et al., "Study of the Interaction Between –Cyclodextrin and Chlorhexidine" *Pharmaceuticals Research*, 11(8): 1207–1210, 1994.

\* cited by examiner

*Primary Examiner*—Thurman K. Page
*Assistant Examiner*—Liliana Di Nola-Baron
(74) *Attorney, Agent, or Firm*—Choate, Hall & Stewart

(57) ABSTRACT

The present invention provides methods of increasing the biological activity of a bioactive agent by complexing the bioactive agent with a complexing agent. In one preferred embodiment, the bioactive agent is an antibiotic and the complexing agent is a cyclodextrin. However, the invention may be extended to include any drugs as bioactive agents. In certain preferred embodiments, the bioactive agent fits into a hydrophobic core of a complexing agent.

6 Claims, 34 Drawing Sheets

FIG.4-1

B. cereus Assay – Chlorhexidine Project

MH (Mueller-Hinton Agar)

| Date: | Agar Content: (%) | Depth (mL) | Pre-diffusion time: | Time in: | Time out: |
|---|---|---|---|---|---|
| 9/20/00 | 1 | 100ml | 4:56 | 5:56 | 10:02 next day |

| Chip#CxDgMBCD Rb503 | | |
|---|---|---|
| Chip Dimensions | | |
| | L (mm) | W (mm) |
| 1 | 2.46 | 1.93 |
| 4 | 2.03 | 1.39 |
| 3 | 1.91 | 1.35 |
| 2 | 2.42 | 2.15 |
| 5 | 2.2 | 1.32 |

TO FIG. 4-3

TO FIG. 4-2

FIG.4-2

FROM FIG.4-1

| Date: | Agar Content: | Depth (mL) | Pre-diffusion time: | Time in: | Time out: |
|---|---|---|---|---|---|
| 9/20/00 | 1 | 100ml | 4:51 | 5:51 | 10:02 next day |

TO FIG. 4-4

Total Length=23cm

| Actisite Dimensions | |
|---|---|
| | L (mm) |
| 1 | 8 |
| 2 | 8.95 |
| 3 | 9.37 |
| 4 | 4.79 |
| 5 | 2.97 |

FIG.4-3

FROM FIG. 4-1

| Date measured: | Drug: | Elliptical n Well | L (mm) |
|---|---|---|---|
| | Cx | 1000 | 16.20 |
| | Cx | 500 | 14.97 |
| | Cx | 200 | 13.56 |
| | Cx | 100 | 12.90 |
| | Cx | 50 | 11.43 |
| | Cx | 25 | 9.90 |
| | Cx | 13 | — |
| | Cx | 1=.0019g | 16.11 |
| | Cx | 4=.0010g | 14.85 |
| | Cx | 3=.0010g | 15.37 |
| | Cx | 2=.0022g | 16.21 |
| | Cx | 5=.0009g | 15.05 |
| | $H_2O$ | Control | — |
| | $H_2O$ | Control | — |

FIG. 4-4

Elliptical n

| Date measured: | Drug: | Well | L (mm) |
|---|---|---|---|
| | Tet | 1000 | 18.64 |
| | Tet | 500 | 17.73 |
| | Tet | 200 | 14.50 |
| | Tet | 100 | 12.21 |
| | Tet | 50 | 10.63 |
| | Tet | 25 | 10.10 |
| | Tet | 12.5 | — |
| | Tet | 1=.0016g | 15.65 |
| | Tet | 2=.0019g | 18.37 |
| | Tet | 3=.0022g | 18.40 |
| | Tet | 4=.0010g | 16.46 |
| | Tet | 5=.0007g | 14.96 |
| | $H_2O$ | Control | — |
| | $H_2O$ | Control | — |

FROM FIG. 4-3
FROM FIG. 4-2
TO FIG. 4-6

FIG. 4-5 measure Radius measure®

| H (mm) | L r (mm) | H r (mm) | Observations |
|---|---|---|---|
| 14.16 | 5.31 | 5.21 | More defined |
| 13.11 | 4.47 | 4.70 | More defined |
| 11.82 | 4.01 | 4.00 | More defined |
| 11.23 | 3.50 | 3.70 | More defined |
| 9.20 | 2.76 | 2.80 | More defined |
| 9.46 | 2.08 | 1.85 | More defined |
| – | – | – | More defined |
| 17.37 | 6.10 | 6.20 | More defined |
| 16.17 | 5.37 | 5.53 | More defined |
| 16.72 | 5.84 | 5.80 | More defined |
| 17.77 | 5.87 | 6.08 | More defined |
| 15.93 | 5.37 | 5.93 | More defined |
| – | – | – | |
| – | – | – | |

FROM FIG. 4-3

FROM FIG.4-5 measure   Radius measure ®

| H (mm) | L r (mm) | H r (mm) | Observations |
|---|---|---|---|
| 16.48 | 6.31 | 6.23 | Less defined |
| 16.01 | 6.20 | 6.25 | Less defined |
| 12.37 | 4.26 | 4.26 | Less defined |
| 10.15 | 3.14 | 3.45 | Less defined |
| 8.71 | 2.22 | 2.10 | Less defined |
| 8.52 | 2.42 | 1.91 | Less defined |
| – | – | – | |
| 14.35 | 5.30 | 4.78 | Less defined |
| 16.30 | 6.30 | 5.44 | Less defined |
| 15.88 | 7.20 | 5.62 | Less defined |
| 15.33 | 6.10 | 6.00 | Less defined |
| 13.89 | 5.53 | 4.83 | Less defined |
| – | – | – | |
| – | – | – | |

FROM FIG. 4-4

*FROM FIG. 4-5*

Clear inhibition zones

| | Analysis | |
|---|---|---|
| | Area = pi * r * r | |
| | Eiliptical measure | |
| Well | Area (A) | Ln (A) X |
| 1000 | 180.2218 | 5.194188 |
| 500 | 154.1891 | 5.03818 |
| 200 | 125.9234 | 4.835673 |
| 100 | 113.8148 | 4.734572 |
| 50 | 82.61581 | 4.414201 |
| 25 | 73.57927 | 4.298363 |
| 13 | #VALUE! | #VALUE! |
| 1=.0019g | 219.849 | 5.392941 |
| 4=.0010g | 188.6538 | 5.239914 |
| 3=.0010g | 201.9014 | 5.307779 |
| 2=.0022g | 226.3078 | 5.421896 |
| 5=.0009g | 188.3568 | 5.238338 |
| Control | #VALUE! | #VALUE! |
| Control | #VALUE! | #VALUE! |

Lysis areas seen

| Well | Eliptical measure Area (A) | Ln (A) X |
|---|---|---|
| 1000 | 241.3416 | 5.486213 |
| 500 | 223.0125 | 5.407228 |
| 200 | 140.9181 | 4.948179 |
| 100 | 97.36678 | 4.578485 |
| 50 | 72.74121 | 4.286908 |
| 25 | 67.60675 | 4.213708 |
| 12.5 | #VALUE! | #VALUE! |
| 1=.0016g | 176.4393 | 5.172977 |
| 2=.0019g | 235.248 | 5.46064 |
| 3=.0022g | 229.5606 | 5.436167 |
| 4=.0010g | 198.2445 | 5.289501 |
| 5=.0007g | 163.2537 | 5.095305 |
| Control | #VALUE! | #VALUE! |
| Control | #VALUE! | #VALUE! |

FROM FIG.4-7
FROM FIG.4-6
TO FIG.4-10

FIG.4-9

| Ln (Q) Y | Predicted | Area (A) |
|---|---|---|
| 6.907755 | 878.4011669 | 86.94034 |
| 6.214608 | 473.0709124 | 66.02288 |
| 5.298317 | 211.8631964 | 50.4073 |
| 4.60517 | 141.8671429 | 40.69667 |
| 3.912023 | 39.80681858 | 24.28601 |
| 3.218876 | 25.14178169 | 12.09272 |
| 2.525729 | #VALUE! | #VALUE! |
| #VALUE! | 1932.398935 | 118.8531 |
| #VALUE! | 1053.092989 | 93.32296 |
| #VALUE! | 1378.425474 | 106.4461 |
| #VALUE! | 2167.603352 | 112.1581 |
| #VALUE! | 1046.532297 | 100.0733 |
| #VALUE! | #VALUE! | #VALUE! |
| #VALUE! | #VALUE! | #VALUE! |

FROM FIG. 4-7

FROM FIG.4-9

FIG.4-10

| Ln (Q) Y | Predicted | Area (A) |
|---|---|---|
| 6.907755 | 801.7558218 | 123.5397 |
| 6.214608 | 658.4442757 | 121.7758 |
| 5.298317 | 209.6409493 | 57.03065 |
| 4.60517 | 83.40341268 | 34.04379 |
| 3.912023 | 40.3156674 | 14.6508 |
| 3.218876 | 33.59039198 | 14.52573 |
| 2.525729 | #VALUE! | #VALUE! |
| #VALUE! | 367.1808317 | 79.61463 |
| #VALUE! | 752.2326293 | 107.7032 |
| #VALUE! | 707.7073946 | 127.1622 |
| #VALUE! | 490.9625609 | 115.0192 |
| #VALUE! | 302.5377791 | 83.93853 |
| #VALUE! | #VALUE! | #VALUE! |
| #VALUE! | #VALUE! | #VALUE! |

FROM FIG. 4-8

| | Radial measure | | |
|---|---|---|---|
| | Ln (A) X | Ln (Q) Y | Predicted |
| | 4.465222 | 6.907755 | 685.82068 |
| | 4.190001 | 6.214608 | 409.91985 |
| | 3.920136 | 5.298317 | 247.47799 |
| | 3.706146 | 4.60517 | 165.86383 |
| | 3.189901 | 3.912023 | 63.168345 |
| | 2.492604 | 3.218876 | 17.14797 |
| | #VALUE! | 2.525729 | #VALUE! |
| | 4.777889 | #VALUE! | 1230.644 |
| | 4.536066 | #VALUE! | 782.96844 |
| | 4.667639 | #VALUE! | 1001.3756 |
| | 4.71991 | #VALUE! | 1104.1978 |
| | 4.605903 | #VALUE! | 892.19467 |
| | #VALUE! | #VALUE! | #VALUE! |
| | #VALUE! | #VALUE! | #VALUE! |

FROM FIG. 4-9

| Radial measure | | |
|---|---|---|
| Ln (A) X | Ln (Q) Y | Predicted |
| 4.816562 | 6.907755 | 673.65377 |
| 4.802181 | 6.214608 | 660.17989 |
| 4.043589 | 5.298317 | 227.41616 |
| 3.527648 | 4.60517 | 110.16139 |
| 2.684495 | 3.912023 | 33.697345 |
| 2.675921 | 3.218876 | 33.293892 |
| #VALUE! | 2.525729 | #VALUE! |
| 4.377198 | #VALUE! | 363.3847 |
| 4.679379 | #VALUE! | 555.5676 |
| 4.845463 | #VALUE! | 701.56829 |
| 4.745099 | #VALUE! | 609.30461 |
| 4.430085 | #VALUE! | 391.41241 |
| #VALUE! | #VALUE! | #VALUE! |
| #VALUE! | #VALUE! | #VALUE! |

FIG.4-13

SUMMARY OUTPUT

| Regression Statistics | |
|---|---|
| Multiple R | 0.989779 |
| R Square | 0.979663 |
| Adjusted R S | 0.974578 |
| Standard Errc | 0.22221 |
| Observations | 6 |

ANOVA

| | df |
|---|---|
| Regression | 1 |
| Residual | 4 |
| Total | 5 |

| | Coefficients |
|---|---|
| Intercept | −13.82628 |
| X Variable 1 | 3.966814 |

Exp (Inter)   9 8929E−07

FROM FIG. 4-11

TO FIG. 4-15

FROM FIG.4-13

FIG.4-14

SUMMARY OUTPUT

| Regression Statistics | |
|---|---|
| Multiple R | 0.984782 |
| R Square | 0.969796 |
| Adjusted R S | 0.962245 |
| Standard Errc | 0.270801 |
| Observations | 6 |

ANOVA

| | df |
|---|---|
| Regression | 1 |
| Residual | 4 |
| Total | 5 |

| | Coefficients |
|---|---|
| Intercept | −6.991221 |
| X Variable 1 | 2.493163 |

Exp (Inter)   0.00091992

FROM FIG. 4-11

| SS | MS | F | ignificance F |
|---|---|---|---|
| 9.51418 | 9.51418 | 192.6837 | 0.000156 |
| 0.197509 | 0.049377 | | |
| 9.711689 | | | |

| Standard Err | t Stat | P-value | Lower 95% | Upper 95% | Lower 95.0% | Upper 95.0% |
|---|---|---|---|---|---|---|
| 1.361165 | -10.15768 | 0.000529 | -17.60549 | -10.04707 | -17.60549 | -10.04707 |
| 0.285772 | 13.88105 | 0.000156 | 3.173383 | 4.760246 | 3.173383 | 4.760246 |

FROM FIG.4-13

| SS | MS | F | ignificance F |
|---|---|---|---|
| 9.418357 | 9.418357 | 128.4325 | 0.000346 |
| 0.293332 | 0.073333 | | |
| 9.711689 | | | |

| Standard Err | t Stat | P-value | Lower 95% | Upper 95% | Lower 95.0% | Upper 95.0% |
|---|---|---|---|---|---|---|
| 1.066151 | -6.557441 | 0.002797 | -9.951337 | -4.031106 | -9.951337 | -4.031106 |
| 0.219995 | 11.33281 | 0.000346 | 1.882357 | 3.103969 | 1.882357 | 3.103969 |

FROM FIG.4-14

SUMMARY OUTPUT

| Regression | Statistics |
|---|---|
| Multiple R | 0.964362 |
| R Square | 0.929994 |
| Adjusted R S | 0.912492 |
| Standard Errc | 0.412273 |
| Observations | 6 |

ANOVA

|  | df | SS | MS |
|---|---|---|---|
| Regression | 1 | 9.031812 | 9.031812 |
| Residual | 4 | 0.679877 | 0.169969 |
| Total | 5 | 9.711689 |  |

|  | Coefficient | Standard Em | t Stat |
|---|---|---|---|
| Intercept | −1.819214 | 0.954023 | −1.906887 |
| X Variable 1 | 1.86997 | 0.256527 | 7.289574 |

| Exp (Inter) | 0.162153 |
|---|---|

FROM FIG. 4-15

SUMMARY OUTPUT

| Regression | Statistics |
|---|---|
| Multiple R | 0.974079 |
| R Square | 0.94883 |
| Adjusted R S | 0.936037 |
| Standard Errc | 0.352473 |
| Observations | 6 |

ANOVA

|  | df | SS | MS |
|---|---|---|---|
| Regression | 1 | 9.21474 | 9.21474 |
| Residual | 4 | 0.496949 | 0.124237 |
| Total | 5 | 9.711689 |  |

|  | Coefficients | Standard Em | t Stat |
|---|---|---|---|
| Intercept | −0.253972 | 0.629753 | −0.403288 |
| X Variable 1 | 1.404879 | 0.163126 | 8.612232 |

Exp (Inter)   0.775713

FIG.4-19

| | F | Significance F |
|---|---|---|
| | 53.13789 | 0.001882 |

| | P-value | Lower 95% | Upper 95% | Lower 95.0% | Upper 95.0% |
|---|---|---|---|---|---|
| | 0.129209 | −4.468012 | 0.829583 | −4.468012 | 0.829583 |
| | 0.001882 | 1.157736 | 2.582203 | 1.157736 | 2.582203 |

FROM FIG.4-17

| F | Significance F |
|---|---|
| 74.17055 | 0.000999 |

| P-value | Lower 95% | Upper 95% | Lower 95.0% | Upper 95.0% |
|---|---|---|---|---|
| 0.707363 | −2.002451 | 1.494506 | −2.002451 | 1.494506 |
| 0.000999 | 0.951968 | 1.857791 | 0.951968 | 1.857791 |

FROM FIG.4-18

Sample analysis

Date:  5/2/97  Patient #:

Calibration

| Standard (Y-range) | Perio (X-range) | Comp. Volume |
|---|---|---|
| 0 | 0 | −0.08 |
| 0.2 | 59 | 0.27 |
| 0.5 | 120 | 0.63 |
| 1 | 164 | 0.88 |
|  |  |  |
|  |  |  |
|  |  |  |
|  |  |  |
|  |  |  |

FROM FIG. 4-19

FROM FIG.4-21

FIG.4-22

Assay:   -Date     Time
            5/3/97

| Standards | | | Area |
|---|---|---|---|
| g(mg) | h | w | |
| 32 | 15.7 | 17.2 | 212.15693 |
| 16 | 13.6 | 15.0 | 160.2726 |
| 8 | 12.3 | 14.0 | 135.28893 |
| 4 | 10.2 | 11.7 | 93.759471 |
| 2 | 8.2 | 9.9 | 63.779067 |
| 1 | 6.6 | 7.8 | 40.445262 |
| 0.5 | 6.0 | 6.8 | 32.05452 |
| 0.25 | 4.0 | 4.0 | 12.5704 |
| 0.125 | ts | ts | #VALUE! |
| | | | |

FROM FIG. 4-20

3  Name:  Alex Tottle

PERIO DATA

| | Rate (ul/min) | Time (sec) | GCF Site |
|---|---|---|---|
| | 0.520 | 60 | 151 |
| | 0.286 | 60 | 255 |
| | 0.544 | 60 | 266 |
| | 0.848 | 60 | 276 |
| | 0.327 | 60 | 353 |
| | 0.490 | 40 | 371 |
| | | | plasma 1 |
| | | | plasma 2 |
| | | | saliva 1 |
| | | | saliva 2 |

FROM FIG. 4-21

DOXYCYCLINE

| Ln A (X) | Ln (Q) (Y) | Predicted | GCF Site |
|---|---|---|---|
| 5.3573262 | 3.4657359 | 20.866853 | 151 |
| 5.0768761 | 2.77258872 | 12.764158 | 255 |
| 4.9074127 | 2.07944154 | 9.4842938 | 266 |
| 4.5407327 | 1.38629436 | 4.9877682 | 276 |
| 4.155425 | 0.69314718 | 2.5388035 | 353 |
| 3.6999495 | 0 | 1.1427299 | 371 |
| 3.4674382 | -0.6931472 | 0.7602693 | plasma 1 |
| 2.5313448 | -1.3862944 | 0.1473871 | plasma 2 |
| #VALUE! | -2.0794415 | #VALUE! | saliva 1 |
| | | | saliva 2 |

FIG. 4-25

| Perio 2h | Volume (microliters) |
|---|---|
| 102 | 0.52 |
| 62 | 0.29 |
| 106 | 0.54 |
| 158 | 0.85 |
| 69 | 0.33 |
| 69 | 0.33 |
| – | 1.00 |
| – | 1.00 |
| – | 1.00 |
| – | 1.00 |

FROM FIG. 4-23

FROM FIG.4-25

FIG.4-26

| 2h / h | h / w | Area | Q | Concen. |
|---:|---:|---:|---:|---:|
| 4.7 | 6.1 | 22.524586 | 0.4096473 | 0.79 |
| 6.8 | 5.9 | 31.520278 | 0.7382012 | 2.58 |
| 7.1 | 6.7 | 37.373371 | 0.9949918 | 1.83 |
| 7.2 | 7.9 | 44.687772 | 1.3610331 | 1.60 |
| 6.3 | 6.9 | 34.152206 | 0.849603 | 2.60 |
| 6.9 | 7.0 | 37.946895 | 1.0219067 | 3.13 |
| 10.6 | 10.3 | 85.777267 | 4.2675645 | 4.27 |
| 10.5 | 10.2 | 84.143115 | 4.1260968 | 4.13 |
| 5.2 | 6.2 | 25.329356 | 0.5031948 | 0.50 |
| 4.9 | 5.6 | 21.558236 | 0.3793447 | 0.38 |

FROM FIG. 4-24

SUMMARY OUTPUT

Regression Statistics

| | |
|---|---|
| Multiple R | 0.96409 |
| R Square | 0.929469 |
| Adjusted R | 0.894203 |
| Standard E | 0.141468 |
| Observatio | 4 |

ANOVA

| | df | SS |
|---|---|---|
| Regressior | 1 | 0.527474 |
| Residual | 2 | 0.040026 |
| Total | 3 | 0.5675 |

| | Coefficients | standard Ern |
|---|---|---|
| Intercept | −0.077426 | 0.120752 |
| X Variable | 0:005859 | 0.001141 |

FROM FIG. 4-25

FROM FIG.4-27

FIG.4-28

SUMMARY OUTPUT

*Regression Statistics*

| | |
|---|---|
| Multiple R | 0.978938 |
| R Square | 0.95832 |
| Adjusted R | 0.951373 |
| Standard E | 0.374404 |
| Observatio | 8 |

ANOVA

| | df | SS |
|---|---|---|
| Regressior | 1 | 19.33796 |
| Residual | 6 | 0.84107 |
| Total | 7 | 20.17903 |

| | Coefficients | standard Ern |
|---|---|---|
| Intercept | −6.351164 | 0.643034 |
| X Variable | 1.752614 | 0.149218 |

| exp(inter.) | 0.0017447 |
|---|---|

FROM FIG. 4-26

| MS | F | ignificance F |
|---|---|---|
| 0.527474 | 26.35631 | 0.03591 |
| 0.020013 | | |

| t Stat | P-value | Lower 95% | Upper 95% | Lower 95.0% | Upper 95.0% |
|---|---|---|---|---|---|
| -0.641197 | 0.587066 | -0.596978 | 0.442127 | -0.596978 | 0.442127 |
| 5.13384 | 0.03591 | 0.000949 | 0.01077 | 0.000949 | 0.01077 |

FROM FIG. 4-27

| MS | F | Significance F |
|---|---|---|
| 19.33796 | 137.9526 | 2.3E-05 |
| 0.140178 | | |

| t Stat | P-value | Lower 95% | Upper 95% | Lower 95.0% | Upper 95.0% |
|---|---|---|---|---|---|
| -9.876869 | 6.22E-05 | -7.924613 | -4.777715 | -7.924613 | -4.777715 |
| 11.74532 | 2.3E-05 | 1.38749 | 2.117738 | 1.38749 | 2.117738 |

FROM FIG.4-29

FROM FIG.4-28

US 6,699,505 B2

METHOD OF INCREASING THE EFFICACY OF ANTIBIOTICS BY COMPEXING WITH CYCLODEXTRINS

PRIORITY INFORMATION

This Application is related to the subject matter in U.S. pending application Ser. No. 09/543,964 filed Apr. 7, 2000 and claims benefit of U.S. Provisional Application No. 60/241,054, filed Oct. 17, 2000. The contents of these applications are incorporated herein by reference.

GOVERNMENT SUPPORT

This invention was made with government support under Grant Numbers NIH-5R01-GM26698 and NIH-1R24-AI47739, awarded by NIH. The United States government has certain rights in the invention.

BACKGROUND OF THE INVENTION

Antibiotics are widely used in medicine for the treatment of infections caused by susceptible microbiological organisms. Many of these drugs have toxic side effects and/or require increased doses for treatment of certain infections. Therefore, there exists the need to develop a system to improve the biological activity of anti-microbials. The applicants have discovered that the biological activity of a bioactive agent may be increased by complexation with cyclodextrin. The cyclodextrin-complexed bioactive agent may be administered to treat infection caused by a susceptible microorganism.

SUMMARY OF THE INVENTION

The present invention relates to the discovery that complexation of a bioactive agent to a complexing agent increases the biological activity of the bioactive agent. Thus, the present invention provides methods of increasing the biological activity of a bioactive agent by complexing the bioactive agent to a complexing agent. In certain preferred embodiments, the bioactive agent is an antibiotic and the complexing agent is a cyclodextrin. In particularly preferred embodiments, a hydrophobic antibiotic, such as chlorhexidine, tetracycline, tobramycin, or gentamicin, is complexed with a cyclodextrin, such as methyl-$\beta$-cyclodextrin or hydroxypropyl-$\beta$-cyclodextrin, to increase the ability of the antibiotic to inhibit microbial growth. Naturally occurring cyclodextrins as well as modified naturally occurring cyclodextrins and chemically modified cyclodextrins may be used in the inventive method.

The present invention further provides methods of treating a microbial infection in an animal by administering to the animal an effective amount of an antibiotic having increased biological activity. According to the teachings of the invention, the biological activity of the antibiotic is increased by complexing it with a cyclodextrin. Those skilled in the art will appreciate that the inventive methods may be extended to other diseases or disorders that are treatable with the appropriate bioactive agent, the activity of which has been increased according to the invention.

DETAILED DESCRIPTION OF CERTAIN PREFERRED EMBODIMENTS

The present invention provides compositions and methods for increasing the biological activity of a bioactive agent by linking the bioactive agent to a complexing agent. The invention is based on the discovery that the attachment of an antibiotic to a complexing agent, specifically a cyclodextrin, increases the biological activity of the antibiotic to a level above that of the uncomplexed antibiotic. The antibiotic/cyclodextrin complexes are suitable for administration to an animal for treatment of a microbial infection. Thus, the invention further provides methods of treating a disease or disorder in an animal (e.g., a mammal, preferably a human) by administering an effective amount of a bioactive agent complexed to a complexing agent, e.g., a cyclodextrin. In one preferred embodiment, the invention provides methods for treating a microbial infection by administering an effective amount of a cyclodextrin-complexed antibiotic.

The data included herein establish that the biological activity of an antibiotic, such as chlorhexidine, can be enhanced by complexing the antibiotic with a cyclodextrin. Without limiting the mechanism of the invention, we propose that the observed enhancement of biological activity is due to an improved interaction of the complexed antibiotic with the bacterial cell wall, which is composed of poly (sugars). Poly(sugars) are likely to interact with the hydrophilic exterior of the cyclodextrin molecule. In addition, an increase in the solubility of the antibiotic may also contribute to the increase in biological activity.

The data disclosed herein relate to chlorhexidine as a model bioactive agent, more particularly to chlorhexidine as a model anti-microbial agent. As but one example, one may use the methods of the invention to improve the potency of a narrow spectrum of antibiotics, e.g., hydrophobic or lipophilic antibiotics. Alternatively or additionally, one may render gram-negative-specific antibiotics active towards gram-positive pathogens. However, the concepts disclosed herein can be extended to many drugs. Accordingly, the present invention may be used to improve the biological activity of any bioactive agent.

Figure 1A:
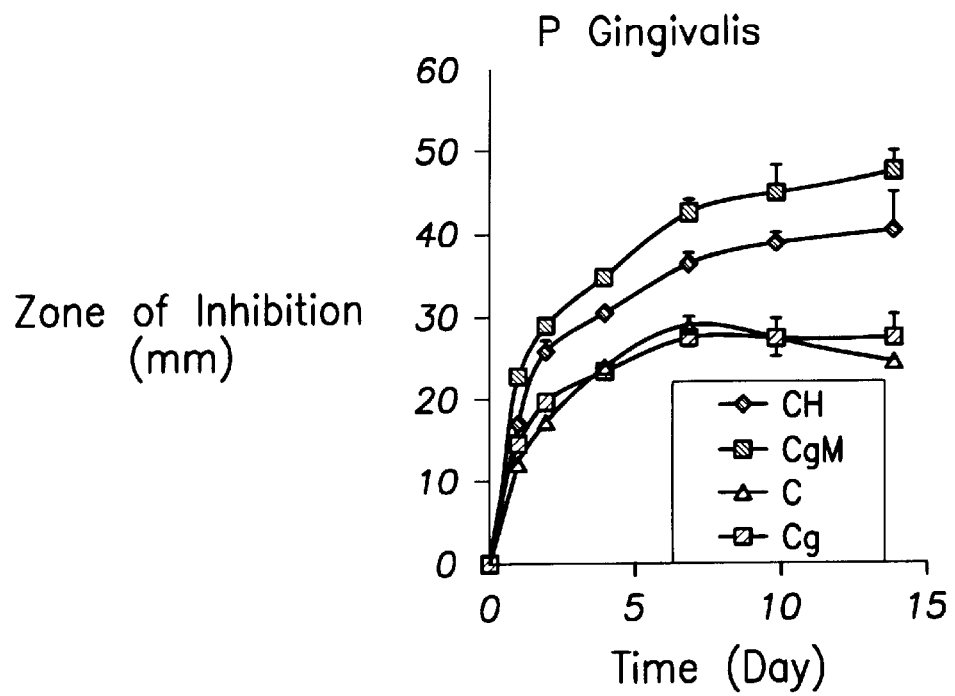
FIG. 1 is a graph showing the effect of complexation of chlorhexidine to cyclodextrin on growth of bacteria over time (*P. gingivalis* (left panel); *B. forsythus* (right panel)). Abbreviations include chlorhexidine (C); chlorhexidine digluconate (Cg); hydroxypropyl-$\beta$-cyclodextrin (H); and methylated-$\beta$-cyclodextrin (M).
Figure 1B:
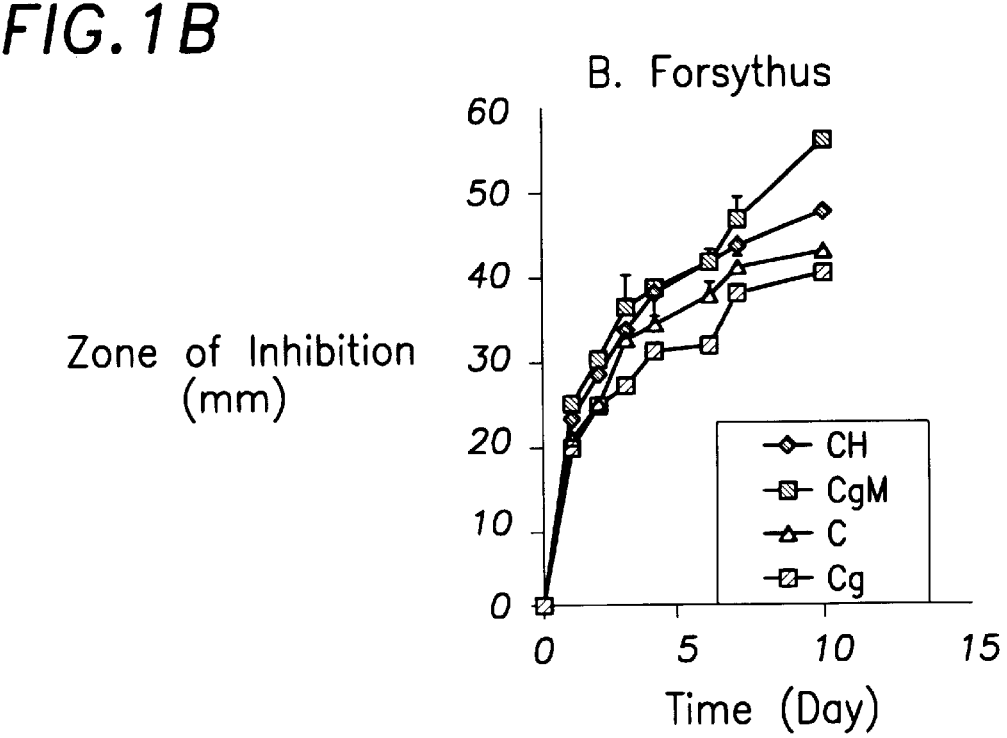

The data demonstrate that complexation of chlorhexidine to the complexing agent cyclodextrin increases the biological activity of the antibiotic by increasing the ability of the antibiotic to inhibit the growth of microorganisms. FIG. 1 is a graph charting the change in size of the zone of growth inhibition of the bacterium *P. gingivalis* over time. The antibiotic being tested (complexed or non-complexed) is applied to a specific point near or within an area of bacterial growth on an agar plate. The bioactive agent diffuses from the application point and causes lysis of already growing bacteria, or inhibition of growth of bacteria within the zone of diffusion. The diameter of bacterial lysis or growth inhibition is a measure of the potency of the bioactive agent. A relatively large zone of lysis or growth inhibition indicates that the antibiotic is relatively potent, i.e., it can result in lysis at very dilute concentrations (on the perimeter of the zone of diffusion). A relatively small zone of lysis or growth inhibition indicates a less biologically active agent.

Figure 2:
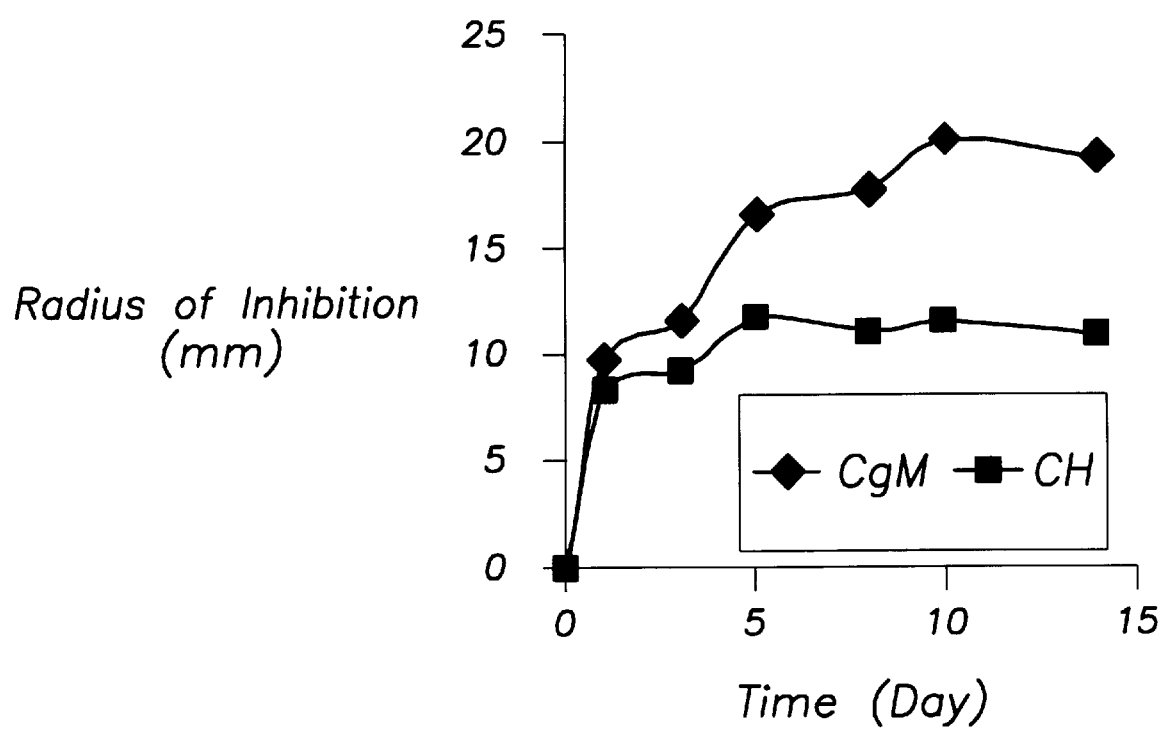
FIG. 2 is a graph of the inhibition showing the effect of complexation of chlorhexidine to cyclodextrin on the growth of the bacteria *P. gingivalis* over time. Abbreviations include chlorhexidine (C); hydroxypropyl-$\beta$-cyclodextrin (H); and methylated-$\beta$-cyclodextrin (M).

Cyclodextrin-complexed chlorhexidine causes larger zones of bacterial growth inhibition than uncomplexed cyclodextrin on both P. gingivalis and B. forsythus (see Example 1). As described above, without limitation, we propose that complexation of chlorhexidine to cyclodextrin may increase the affinity of the antibiotic to the bacteria via improved interaction with the bacterial cell wall. FIG. 2 similarly demonstrates the increased biological activity of cyclodextrin-complexed chlorhexidine.

The spread sheet compares a known commercial system called Actisite (tetracycline delivery from poly(propylene) fibers) with our cyclodextrin-complexed chlorhexidine and derivatives.

Complexing Agents

Figure 3:
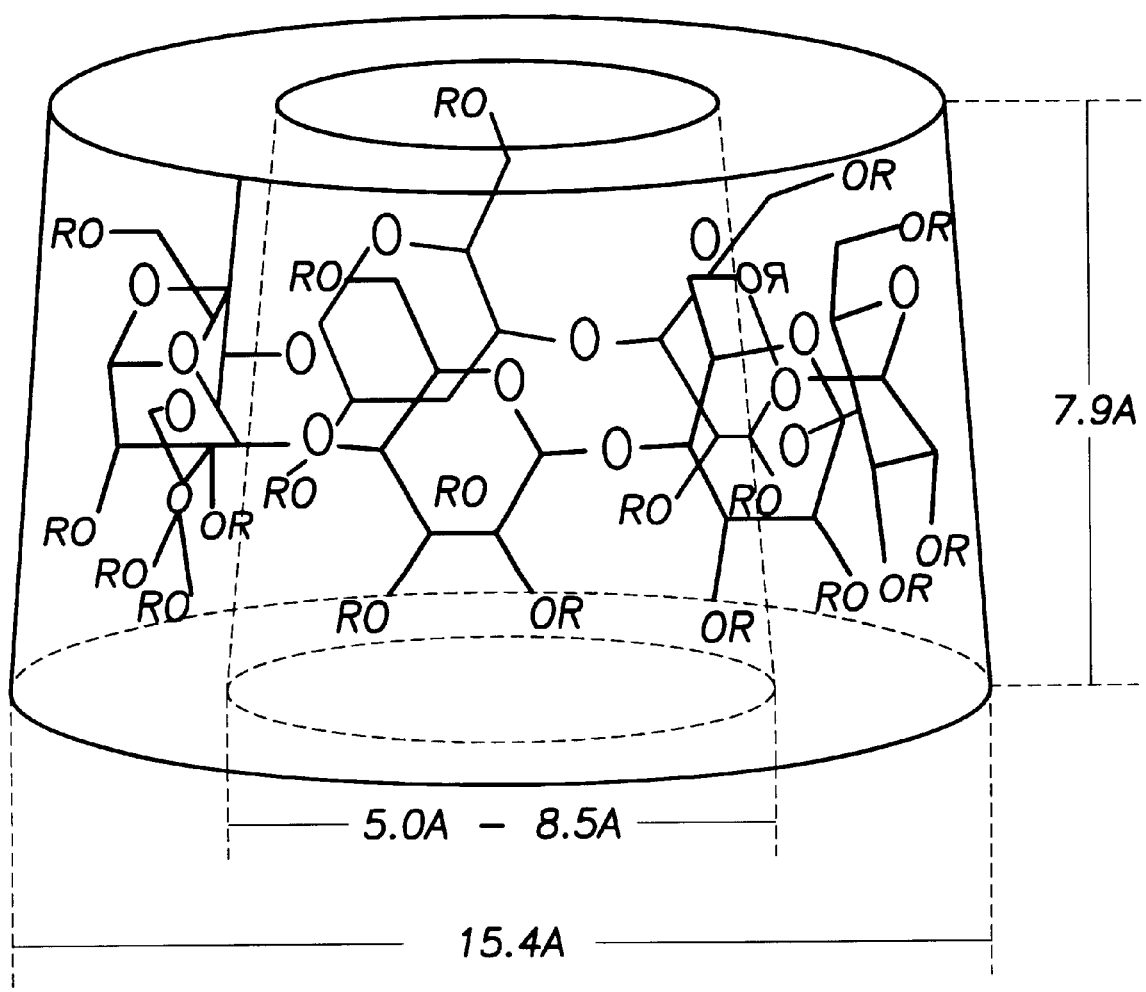
FIG. 3 is a structural diagram of $\beta$-cyclodextrin.

In preferred embodiments, the complexing agent has a hydrophobic core and a hydrophilic exterior. A suitable complexing agent is β-cyclodextrin, which may be methyl-β-cyclodextrin, hydroxypropyl-β-cyclodextrin, or any derivative thereof. Cyclodextrins are relatively large cyclic carbohydrates that are conical in shape. FIG. 3 illustrates the structure of β-cyclodextrin showing the hydrophobic core and the hydrophilic exterior. This structure can form supramolecular inclusion host-guest particles, wherein cyclodextrin is the host molecule and the bioactive agent is the guest molecule residing within the hydrophobic core of cyclodextrin. The host-guest complex may be generated by physically mixing the cyclodextrin molecule with the bioactive agent.

Those skilled in the art will appreciate that both natural and chemically modified cyclodextrins are readily available in the art and may be used in the present invention to increase the biological activity of a bioactive agent (see "Comprehensive Supramolecular Chemistry" Volume 3, edited by József Szejtili and Tetsuo Osa, published by Elsevier Science Inc., New York, N.Y.). Naturally occurring cyclodextrins include α-, β-, and γ-cyclodextrins (Pagington, *Chemistry in Britain*, 23:455 (1987); Parrish, *Cyclodextins-A Review*, Stering Organics Ltd. Newcastel-Upon-Tyne. England; Szejtli, *Cyclodextrin Technology: Topics in Inclusion Science*, Kluwer Academic Publishers (1988)). Modifications of natural cyclodextrins can also easily be made and include, for example, glucosyl-α-cyclodextrin, maltosyl-α-cyclodextrin, glucosyl-β-cyclodextrin, and maltosyl-β-cyclodextrin.

Those skilled in the art will further appreciate that many different chemical moieties may be introduced into the cyclodextrin molecule and such chemically modified cyclodextrins are readily available (see, e.g., Yoahida et al., *Int. Pharm.*, 46:217 (1988); Muller et al., *J. Pharm. Sci.* 75(6): June 1986;; Irie et al., *Pharm. Res.*, No. 11, p. 713 (1988)). As but one example, chemically modified cyclodextrins may be generated by reaction of the hydroxyl groups lining the upper and lower ridges of the toroid of cyclodextrin with, for example, methyl, hydroxyethyl, hydoxylpropyl, carboxymethyl, or acetyl. Each cyclodextrin hydroxyl group differs in its chemical reactivity so that the reaction process produces an amorphous mixture of thousands of positional and potical isomers. The hydroxypropyl-β-cyclodextrin system is a highly complex mixture of various isometric forms of variously substituted β-cyclodextrin derivatives. This property of amorphousness is important to certain phsio-chemical properties of the chemically modified cyclodextrins and has beneficial effects on aqueous solubility and toxicity of the crystalline parent molecule (Yoshida et al., supra; Muller et al., supra; Irie et al., supra; Muller et al., *Pharm Res.* 10:309 (1985)).

Those skilled in the art will appreciate that both modified natural cyclodextrins and chemically modified derivatives of cyclodextrin may be used to optimize the bioactivity of a bioactive agent. Formulations may be further optimized by derivatization of a cyclodextrin molecule to optimize the concentration, storage, manufacturing requirements, or route of administration of the bioactive agent.

Bioactive Agents

In certain preferred embodiments, the bioactive agents of the invention are antibiotics. The term antibiotic is used according to Tabers Cyclopedic Medical Dictionary, $15^{th}$ Ed. to describe antimicrobial substances which have the ability to inhibit the growth of or to destroy microorganisms. These substances are active in dilute solutions and may be produced in whole or in part by a microorganism or by a synthetic or semi-synthetic method. Hydrophobic antibiotics are particularly preferred as they will insert into the hydrophobic core of a complexing agent, e.g., a cyclodextrin.

Antibiotics that are useful in the present invention include penicillin derivatives such as penicillin G, penicillin V, penicillin G benzathine, ampicillin, anoxacillin, nafcillin, carbenicilllin, dicloxacillin, bacampicillin, piperacillin, ticaricillin, mezlocillin and the like; cephalosporins such as cefazolin, cefadroxil, cephalexin, cefaclor, cefoxitin, cefonicid, ceftizoxime, cefprozil, ceftazidine, cefixime, cefpodoxime proxitel and the like; aminoglycosides such as amikacin, gentamicin, tobramycin, netilmicin, streptomycin and the like; macrolides such as erythromycin and the like; monobactams such as aztreonam and the like; rifamycin and derivatives such as rifampin, rifamide, rifaximin and the like; chloramphenicol, clindamycin, lincomycin; imipenem; vancomycin; tetracyclines such as chloretetracycline, tetracycline, minocycline, doxycycline and the like; fusidic acid, novobiocin and the like; fosfomycin, fusidate sodium, neomycin, bacitracin, polymyxin, capreomycin, colistimethate, colistin and gramicidin. In addition, cyclodextrin may be complexed with more than one antibiotic and/or combined with other antibacterial agents. Suitable combinations include:

rifampin+erythromycin
erythromycin+sulfonamide such as sulfisoxazole
penicillin+streptomycin
rifampin+beta lattamin
rifamin+fluoroquinolones
rifampin+vancomycin
rifampin+tetracyclines
rifampin+timetoprim
novobiocin+fluoroquinolones
trimetoprim+sulfonamides
rifampin+fusidic acid
rifampin+isoniazid
rifampin+fosfomycin
rifampin+clofazmin+dapsone
rifampin+aminoside
vancomycin+fusidic acid.

Many of the antimicrobial drugs are described in Remingtons Pharmaceutical Sciences, 15th Ed., Chapter 64, which is incorporated by reference.

The definition of "bioactive agent" according to the present invention may be extended to include many other drugs. Based on the discovery of the invention, those skilled in the art will appreciate that complexation of cyclodextrin to other bioactive agents may increase their biological activity as it increases the biological activity of the antibiotic chlorhexidine. Suitable bioactive agents include but are not limited to drugs that are proteins, polypeptides, polynucleotides, nucleoproteins, polysaccharides, glycoproteins, lipoproteins, and synthetic and biologically engineered analogs thereof.

Testing multiple bioactive agents for this effect would be routine to the skilled artisan. One would simply compare the biological activity of the complexed and uncomplexed bioactive agent using a biological assay specific for the particular bioactive agent. Such an assay would be standard if the bioactive agent is, for example, a commercially available pharmaceutical drug for which the biological activity has been well-established. An increase in biological activity of the complexed bioactive agent, compared to the uncomplexed bioactive agent, indicates that the complexing agent increases the biological activity of the bioactive agent.

Bioactive agents for use in the present invention include any pharmacologically active substances that produce a local or systemic effect in animals, preferably mammals, or humans. The term thus means any substance intended for use in the diagnosis, cure, mitigation, treatment or prevention of disease or in the enhancement of desirable physical or mental development and conditions in an animal or human. Examples of bioactive agents that might be utilized in the methods of the invention include literally any bioactive agent, preferably hydrophobic bioactive agents. Preferably, though not necessarily, the drug is one that has already been deemed safe and effective for use by the appropriate governmental agency or body. For example, drugs for human use listed by the FDA under 21 C.F.R. §§ 330.5, 331 through 361; 440–460; drugs for veterinary use listed by the FDA under 21 C.F.R. §§ 500–582, incorporated herein by reference, are all considered acceptable for use in the present method.

Classes of pharmaceutically active compounds that can be used in the practice of the present invention include, but are not limited to, anti-AIDS substances, anti-cancer substances, antibiotics, immunosuppressants (e.g., cyclosporine), anti-viral substances, enzyme inhibitors, neurotoxins, opioids, hypnotics, antihistamines, lubricants, tranquilizers, anticonvulsants, muscle relaxants and anti-Parkinson substances, anti-spasmodics and muscle contractants, miotics and anti-cholinergics, anti-glaucoma compounds, antiparasite and/or anti-protozoal compounds, antihypertensives, analgesics, anti-pyretics and anti-inflammatory agents such as NSAIDs, local anesthetics, ophthalmics, prostaglandins, anti-depressants, antipsychotic substances, anti-emetics, imaging agents, specific targeting agents, neurotransmitters, proteins, cell response modifiers, vaccines, ribozymes, anti-sense agents, and RNA.

A more complete listing of classes of compounds suitable for delivery into cells according to the present invention may be found in the Pharmazeutische Wirkstoffe (Von Kleemann et al. (eds) Stuttgart/New York, 1987, incorporated herein by reference). Examples of particular pharmaceutically active substances are presented below:

Anti-AIDS substances are substances used to treat or prevent Autoimmune Deficiency Syndrome (AIDS). Examples of such substances include, but are not limited to, CD4, 3'-azido-3'-deoxythymidine (AZT), 9-(2-hydroxyethoxymethyl)-guanine (acyclovir), phosphonoformic acid, 1-adamantanamine, peptide T, and 2',3'dideoxycytidine.

Anti-cancer substances are substances used to treat or prevent cancer. Examples of such substances include, but are not limited to, methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. As described above, examples of antibiotics include, but are not limited to, penicillins, aminoglycosides, macrolides, monobactams, rifamycins, tetracyclines, chloramphenicol, clindamycin, lincomycin, imipenem, fusidic acid, novobiocin, fosfomycin, fusidate sodium, neomycin, polymyxin, capreomycin, colistimethate, colistin, gramicidin, minocycline, doxycycline, vanomycin, bacitracin, kanamycin, gentamycin, erythromicin and cephalosporins.

Anti-viral agents are substances capable of destroying or suppressing the replication of viruses. Examples of anti-viral agents include, but are not limited to, α-methyl-P-adamantane methylamine, 1,-D-ribofuranosyl-1,2,4-triazole-3 carboxamide, 9-[2-hydroxy-ethoxy] methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include, but are not limited to, edrophonium chloride, N-methylphysostigmine, neostigmine bromide, physostigmine sulfate, tacrine HCl, tacrine, 1-hydroxy maleate, iodotubercidin, p-bromotetramisole, 10-(alpha-diethylaminopropionyl)-phenothiazine hydrochloride, calmidazolium chloride, hemicholinium-3, 3,5-dinitrocatechol, diacylglycerol kinase inhibitor I, diacylglycerol kinase inhibitor II, 3-phenylpropargylamine, $N_6$-monomethyl-L-arginine acetate, carbidopa, 3-hydroxybenzylhydrazine HCl, hydralazine HCl, clorgyline HCl, deprenyl HCl,L(−)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate,R(+)-, p-aminoglutethimide tartrate, S(−)-, 3-iodotyrosine, alpha-methyltyrosine, L-, alpha-methyltyrosine, D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include, but are not limited to, adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4-phenyl-1,2,5,6-tetrahydropyridine HCl, 1-methyl-4-phenylpyridinium iodide.

Opioids are substances having opiate like effects that are not derived from opium. Opioids include opioid agonists and opioid antagonists. Opioid agonists include, but are not limited to, codeine sulfate, fentanyl citrate, hydrocodone bitartrate, loperamide HCl, morphine sulfate, noscapine, norcodeine, normorphine, thebaine. Opioid antagonists include, but are not limited to, nor-binaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include, but are not limited to, pentobarbital sodium, phenobarbital, secobarbital, thiopental and mixtures, thereof, heterocyclic hypnotics, dioxopiperidines, glutarimides, diethyl isovaleramide, a-bromoisovaleryl urea, urethanes and disulfanes.

Antihistamines are substances which competitively inhibit the effects of histamines. Examples include, but are not limited to, pyrilamine, chlorpheniramine, tetrahydrazoline, and the like.

Lubricants are substances that increase the lubricity of the environment into which they are delivered. Examples of biologically active lubricants include, but are not limited to, water and saline.

Tranquilizers are substances which provide a tranquilizing effect. Examples of tranquilizers include, but are not limited to, chloropromazine, promazine, fluphenzaine, reserpine, deserpidine, and meprobamate.

Anti-convulsants are substances which have an effect of preventing, reducing, or eliminating convulsions. Examples of such agents include, but are not limited to, primidone, phenytoin, valproate, Chk and ethosuximide.

Muscle relaxants and anti-Parkinson agents are agents which relax muscles or reduce or eliminate symptoms associated with Parkinson's disease. Examples of such agents include, but are not limited to, mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include, but are not limited to, atropine, scopolamine, oxyphenonium, and papaverine.

Miotics and anti-cholinergics are compounds which cause bronchodilation. Examples include, but are not limited to, echothiophate, pilocarpine, physostigmine salicylate, diisopropylfluorophosphate, epinephrine, neostigmine, carbachol, methacholine, bethanechol, and the like.

Anti-glaucoma compounds include, but are not limited to, betaxalol, pilocarpine, timolol, timolol salts, and combinations of timolol, and/or its salts, with pilocarpine.

Anti-parasitic, -protozoal and -fungals include, but are not limited to, ivermectin, pyrimethamine, trisulfapyrimidine, clindamycin, amphotericin B, nystatin, flucytosine, natamycin, and miconazole.

Anti-hypertensives are substances capable of counteracting high blood pressure. Examples of such substances include, but are not limited to, alpha-methyldopa and the pivaloyloxyethyl ester of alpha-methyldopa.

Analgesics are substances capable of preventing, reducing, or relieving pain. Examples of analgesics include, but are not limited to, morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include, but are not limited to, aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include, but are not limited to, procaine, lidocain, tetracaine and dibucaine.

Ophthalmics include diagnostic agents such as sodium fluorescein, rose bengal, methacholine, adrenaline, cocaine, and atropine. Ophthalmic surgical additives include, but are not limited to, alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include, but are not limited to, imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include, but are not limited to, phenothiazines, butyrophenones and thioxanthenes.

Anti-emetics are substances which prevent or alleviate nausea or vomiting. An example of such a substance includes, but is not limited to, dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include, but are not limited to, agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include, but are not limited to, dopamine, serotonin, q-aminobutyric acid, norepinephrine, histamine, acetylcholine, and epinephrine.

Cell response modifiers are chemotactic factors such as platelet-derived growth factor (PDGF). Other chemotactic factors include, but are not limited to, neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein.

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins.

Uses

Those of ordinary skill in the art will immediately appreciate that the present invention can be utilized in a wide variety of applications to increase the biological activity of bioactive agents. Bioactive agents having increased biological activity are likely to be more potent both in vivo and in vitro. For example, a complexed bioactive agent may have an improved effectiveness in a biological assay at the same dose as an uncomplexed bioactive agent. More particularly, bioactive agents, e.g., antibiotics and other drugs, having an increased biological activity are useful in vivo for the treatment of disease. Increasing the biological activity of a drug reduces the dose required to achieve a desired biological effect. This is advantageous in that the effective dose of many bioactive agents causes toxic side effects in vivo. Side effects may range from mild to severe and may, in some cases, preclude use of the drug. Reducing the dose of the bioactive agent may result in reduced in vivo toxicity. Increasing the biological activity of a bioactive agent may also result in improved effectiveness of the compound in vivo. For example, a maximum dose of a particular antibiotic may have limited effectiveness in vivo for eradicating a particular microorganism responsible for an infection. However, the same maximum dose of an antibiotic having increased biological activity due to complexation with a cyclodextrin may eliminate the infection entirely.

Pharmaceutical Compositions

As will be appreciated by one of ordinary skill in the art, pharmaceutical compositions may be constituted into any form suitable for the mode of administration selected. Cyclodextrins may be administered by every route of administration possible. The main causes of toxicity by the cyclodextrins are related to effects on sensitive cell membranes and bulk effects (such as precipitation). Almost all cyclodextrins are safe for topical use because there is no danger of the cyclodextrin getting past the outer skin barrier. Topical uses such as eye drops, suppositories (vaginal and rectal), nasal inhalants, and the like have the possibility of getting beyond the dermal barrier, but may be easily tested for irritation and systemic residuals. Bioactive agents that are complexed to a cyclodextrin may be easily tested for toxic in vivo effects.

According to the invention, cyclodextrin-complexed bioactive agents having increased biological activity may be administered in an effective amount to patients in need of treatment. More particularly, the complexed bioactive agents may be administered in various forms. For example, the complexed bioactive agent may be mixed with an excipient and used as an oral administration and/or a non-oral administration. Alternatively, the complexed bioactive agent may be mixed in suitable proportions with supplementary substances such as lubricating agents, emulsifying agents, dispersing agents, and the like.

For in vivo delivery (i.e., to a patient with a bacterial infection), it is preferred that the delivery agent be biocompatible and preferably biodegradable and non-immunogenic. In addition, it is desirable to deliver a therapeutically effective amount of a compound in a physiologically acceptable carrier. For example, it is known that one may inject a compound into a patient in a buffered saline solution. Injection into an individual may occur intravenously, intramuscularly, or, for example, directly into a tumor. Alternatively, in vivo delivery may be accomplished by use of a syrup, an elixir, a liquid, a tablet, a pill, a time-release capsule, an aerosol, or a transdermal patch.

As an oral administration, the complexed bioactive agent may be administered in the form of a pill, liquid (solutions, syrups, elixirs, and suspensions), powder, tablet, capsule, granules etc. and in such cases, the excipients used are, apart from water, sugar, starch, dextran, calcium phosphate, calcium carbonate, magnesium oxide, magnesium stearate, aluminium silicate, aluminiium hydroxide, sodium bicarbonate, glycerin etc. Carriers are intended to include necessary and inert bindings, suspending agents, lubricants, flavorants, sweeteners, preservatives, dyes, and coatings.

As a non-oral administration, it may be in the form of an injection, a drip, an ointment etc. and it may be mixed with a common substance such as distilled water, phsiological saline, vegetable oils, such as olive oil etc., alcohol such as ethanol etc., polyethylene glycol and so on. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular patient being treated will result in a need to adjust dosages, including patient age, weight, gender, diet, and time of administration.

EXAMPLES

Example 1

Inhibition of Bacterial Growth

Comparison of Bacteria Growth Inhibition of Drug, Drug Complex, and Complex Components Materials Trypticase Soy Agar, Becton Dickinson and Company Brain Heart Infusion, Becton Dickinson and Company Yeast Extract, Becton Dickinson and Company MilliQ water Hemin (100x), Sigma Chemicals Defibrinated Sheep Blood, Binax Laboratories Vitamin K, Sigma Chemicals N-acetylmuramic acid, Sigma Chemicals Teflon well forming device, Massachusetts Institute of Technology Electronic Digital Calipers, VWR Scientific Hydroxypropyl (H) and methylated beta-cyclodextrin (M), Cerestar Company Chlorhexidine (C) and Chlorhexidine Digluconate (Cg), Degussa Chemicals Poly(dl-lactic-co-glycolic)acid (PLGA), BI Chemicals

*B. forsythus* and *P. gingivalis*, Goodson Laboratory, Forsyth Institute

Methods

Increased biological activity of the antibiotic chlorhexidine was tested by placing chips composed of chorhexidine (C) and clorhexidine digluconate (Cg) complexed with hydroxypropyl-β-cyclodextrin (H) or methylated β-cyclodextrin adjacent to a tooth in agar seeded with *P. gingivalis* or *B. forsythus*. The agar plates were incubated to allow growth of the bacterium for 12–15 days and the zone of inhibition of bacterial growth around each chip was measured. An increase in biological activity was measured by an increase in the size of the zone of inhibition around the chip containing the complexed antibiotic compared to the size of the zone around the chip containing the uncomplexed antibiotic.

More particularly, the method used the following steps:

Mix: 5 g Trypticase Soy Agar
    6.5 g Brain Heart Infusion
    2.5 g Yeast Extract
    250 mL MilliQ water
    2.5 mL Hemin (100x).
Autoclave mixture for 15 minutes at 121 degree Celsius.
Cool to 50 degrees Celsius for 1 hour.
Add: 12.5 mL defibrinated sheep blood.
2.5 mL Vitamin K (100x).
300 uL N-acetylmuramic acid (100x).
Prepared *B. forsythus* and *P. gingivalis* culture solution with an optical density of 1~$10^9$ cells/mL.
Added 2 mL of bacteria culture into their respective agar solutions.
Pour 20 mL agar solution into 150 mm diameter petri dishes.
Place well former into petri dishes.
Allow agar to harden by cooling to room temperature for 1 hour.
Place petri dishes in anaerobic chamber at 37° C. in an atmosphere consisting of 80% nitrogen, 10% hydrogen, and 10% carbon dioxide for 2 days.
Place 4 mm×5 mm×0.5 mm PLGA chips composed of: Cg, C, C/H, Cg/M, M, and H into preformed wells.
Masses of each component based on 25 wt % of Cg with respect to a 10 mg chip.
Add MilliQ water into wells to keep chips hydrated.
Keep petri dishes in anaerobic chamber during entire experiment.
Measure zones of inhibition daily using electronic calipers from the center of the well.
Experiments done in triplicate.

Results

The drug/sugar complex and its individual components were placed on NHK plates of *P. gingivalis* and *B forsythus* to compare inhibition zones. The diameters of the zones of inhibition were measured using an electronic caliper. PLGA and cyclodextrins were tested for anti-microbial activity individually and demonstrated no inhibition of the bacteria species.

All polymeric chips containing C or its derivatives demonstrated a clear zone of inhibition beginning on the first day. Use of sugar complexation resulted in larger zones of bacterial inhibition than without complexation for both periodontal disease causing bacteria, *P. gingivalis* and *B. forsythus*. It was observed that polymeric chips containing C and Cg showed zones of inhibition that were statistically similar. In both bacterial species studied, polymeric chips composed of Cg/M complex demonstrated the larger zone of inhibition than chips composed of C/H.

As shown in FIG. 1 (left panel) complexation of cyclodextrin to chlorhexidine (hydroxypropyl-β-cyclodextrin or methylated β-cylcodextrin) results in approximately a 50% increase in biological activity, which correlates to about a 50% increase in the size of the zone of inhibition of the cyclodextrin-complexed chlorhexidine compared to the uncomplexed chlorhexidine. Similar result are shown in the right panel of FIG. 1, where methylated cyclodextrin-complexed chlorhexidine exhibits about a 30% increase in biological activity compared to uncomplexed chlorhexidine (chlorhexidine digluconate). A smaller increase in the zone of inhibition (from about 40 mm to about 45 mm) was observed between hydroxypropyl-β-cyclodextrin-complexed chlorhexidine and uncomplexed chlorhexidine.

BACTERIA INHIBITION STUDY USING NATURAL TEETH

Materials

Extracted maxillary $1^{st}$ to $3^{rd}$ molars due to large palatal root surface
Trypticase Soy Agar, Becton Dickinson and Company
Brain Heart Infusion, Becton Dickinson and Company
Yeast Extract, Becton Dickinson and Company
MilliQ water
Hemin (100x), Sigma Chemicals
Defibrinated Sheep Blood, Binax Laboratories
Vitamin K, Sigma Chemicals
N-acetylmuramic acid, Sigma Chemicals
Hydroxypropyl (H) and methylated beta-cyclodextrin (M), Cerestar Company
Chlorhexidine (C) and Chlorhexidine Digluconate (Cg), Degussa Chemicals
Poly(dl-lactic-co-glycolic)acid (PLGA), BI Chemicals
*P. gingivalis*, Goodson Laboratory, Forsyth Institute Methods Mix: 5 g Trypticase Soy Agar
    6.5 g Brain Heart Infusion
    2.5 g Yeast Extract
    250 mL MilliQ water
    2.5 mL Hemin (100x).
Autoclave mixture for 15 minutes at 121 degree Celsius.
Cool to 50 degrees Celsius for 1 hour.
Add: 12.5 mL defibrinated sheep blood
    2.5 mL Vitamin K (100x)
    300 uL N-acetylmuramic acid (100x).
Prepared *P. gingivalis* culture solution with an optical density of 1~$10^9$ cells/mL.
Added 2 mL of bacteria culture into their respective agar solutions.
Pour 20 ml of agar solution into 150 mm diameter petri dishes.
Extracted molars were autoclaved.
Sterilized tooth placed in agar during solidification.
Allow agar to harden by cooling to room temperature for 1 hour.
Place petri dishes in anaerobic chamber at 37° C. in an atmosphere consisting of 80% nitrogen, 10% hydrogen, and 10% carbon dioxide for 2 days.
Place 10 mg 4 mm×5 mm×0.5 mm PLGA chips composed of C/H and Cg/M vertically directly adjacent to the tooth root.
Keep petri dishes in anaerobic chamber during entire experiment.
Measure zones of inhibition daily using electronic calipers from the center of the well.

Results

Polymeric chips containing Cg/M complex and C/H complex were placed vertically adjacent to a sterilized tooth in agar seeded with *P. gingivalis*. Zones of inhibition were larger in the chips containing Cg/M complex than C/H complex that progressively increased or was sustained until day 15. The results are shown in FIG. 2. An excellent zone of inhibition was observed from day 1 that progressively increased or was sustained until day 15.

COMPARISON STUDY WITH ACTISITE

Materials

Mueller-Hinton Broth, Sigma Chemicals

*B. cereus*, Goodson Laboratory, Forsyth Institute

Agar, Becton Dickinson and Company

Teflon well forming device, produced at Massachusetts Institute of Technology

Electronic Digital Caliper, VWR Scientific

Hydroxypropyl (H) and methylated beta-cyclodextrin (M), Cerestar Company

Chlorhexidine (C) and Chlorhexidine Digluconate (Cg), Degussa Chemicals

Poly(dl-lactic-co-glycolic)acid (PLGA), BI Chemicals

Actisite: generous gift from P&G/ALZA Corporation

Methods

Prepared Mueller-Hinton Broth at 22 g/L of MilliQ water.

Add 1.5 g of fresh agar to broth.

Autoclaved for 15 minutes at 121 degrees Celsius.

Cool to 50 degrees Celsius for 1 hour.

Prepared *B. cereus* culture solution with an optical density of $1\sim10^9$ cells/mL.

Add 2 mL of *B. cereus* culture into agar.

Pour 20 mL of agar solution into 150 mm diameter petri dishes.

Place well former into petri dishes.

Allow agar to harden by cooling to room temperature for 1 hour.

Weigh Cg/M chips and Actisite Fibers at equivalent masses.

Place chips, fibers, and standards into preformed wells in hardened agar.

Cover chips with MilliQ water.

Incubate in anaerobic chamber at 37° C. in an atmosphere consisting of 80% nitrogen, 10% hydrogen, and 10% carbon dioxide.

Measure zones of inhibition using electronic calipers from the center of the well.

Sensitive Assay:

Gordon, J. M., Walker, C. B., Goodson, J. M., and Socransky, S. S. 1980. Sensitive assay for measuring tetracycline levels in gingival crevice fluid. Antimicrobial Agents & Chemotherapy 17: 193–198, incorporated herein by reference.

Results

Figure 4:
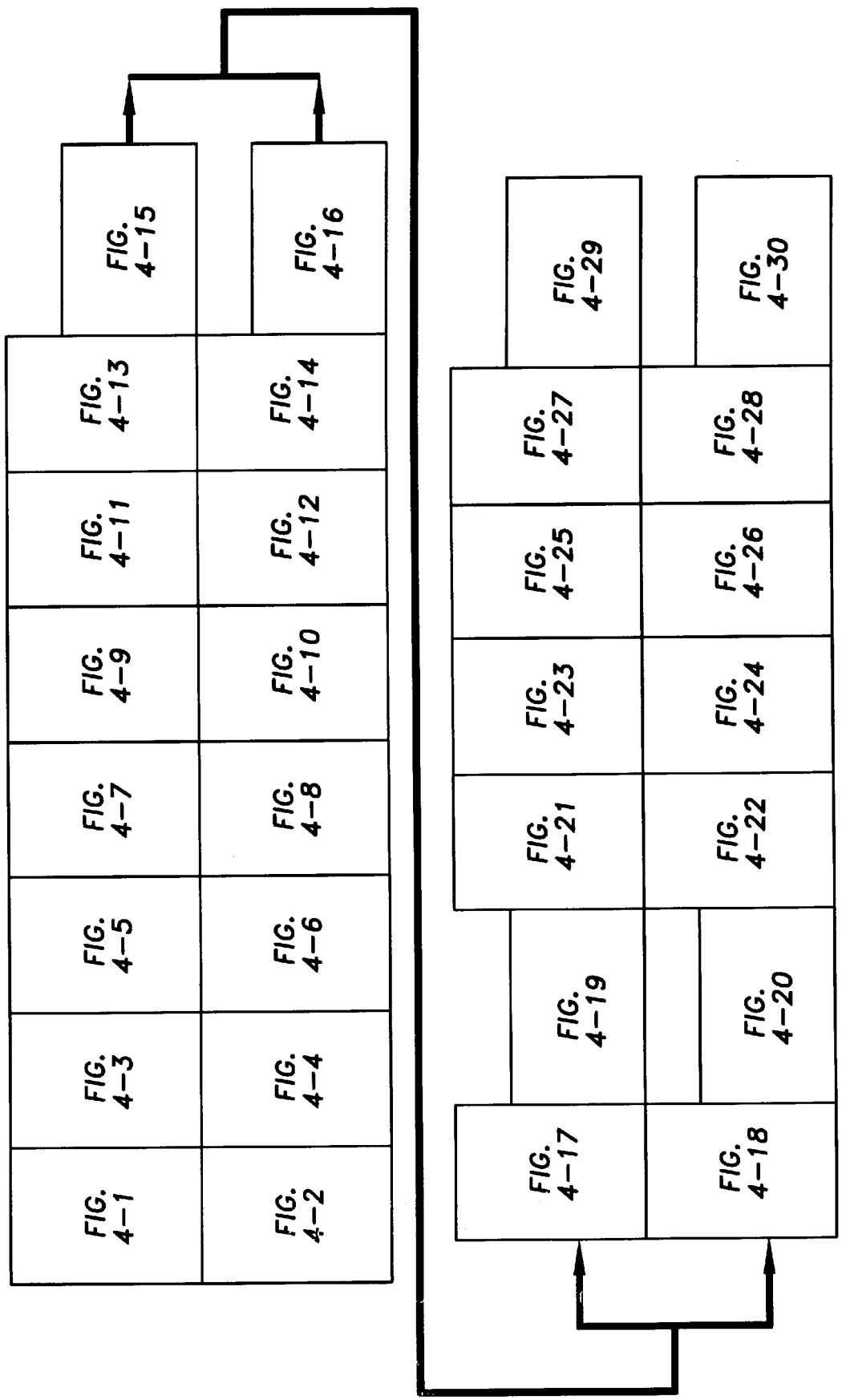
FIG. 4 is a series of tables illustrating the increased biological activity of a chlorhexidine complexed to cyclodextrin compared to uncomplexed antibiotics Page 1: Cx=chlorhexidine digluconate, Tet=tetracycline, Well=quantity of reagent added to well, L=zone of inhibition. In the boxes on page 1 of FIG. 4, L=length of chip containing reagent, W=width of chip containing reagent. Page 2 Lr is the radius of the zone of inhibition or lysis minus the size of the chip; Hr is the radius of the zone of inhibition or lysis minus the size of the chip; A is the area of the zone of inhibition or lysis. Page 3 shows the predicted inhibition (Predicted) using the Gordon et al formula; top panel is chlorhexidine, bottom panel is actisite (tetracycline).

Actisite (Tetracycline) fibers and Cg/M complexed chips were compared at approximately equivalent total and drug masses. As shown in FIG. 4, it was observed that the zones of inhibition for Cg/M complexed chips were more defined than zones of inhibition for the Actisite fibers. Using the Sensitive Assay, calculations predicted that chips made of Cg/M complex were more effective at reaching a higher level of bacterial inhibition.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of increasing the biological activity of an antibiotic selected from the group consisting of chlorhexidine, chlorhexidine digluconate, tobramycin, and gentamicin, comprising the steps of complexing the antibiotic to a cyclodextrin selected from the group consisting of hydroxypropyl-β-cyclodextrin and methylated-β-cyclodextrin, wherein the zone of inhibition around a chip containing the antibiotic/cyclodextrin complex is at least 30% greater than the zone of inhibition of an uncomplexed antibiotic.

2. The method of claim 1, wherein cyclodextrin is chemically modified.

3. A method of treating a microbial infection in an animal comprising administering to the animal an effective amount of chlohexidine that is complexed to methylated-β-cylodexirin.

4. The method of claim 3, wherein the chlorhexidine is chemically modified.

5. A method of treating a microbial infection in an animal comprising administering to the animal an effective amount of a hydrophobic antibiotic selected from the group consisting of chlorhexidine digluconate, tobramycin, and gentamicin that is complexed to a cyclodextrin selected from the group consisting of hydroxypropyl-β-cyclodextrin and methylated-β-cyclodextrin.

6. The method of claim 5, wherein the cyclodextrin is chemically modified.

* * * * *